US00PP18919P2

(12) United States Plant Patent
Olesen

(10) Patent No.: US PP18,919 P2
(45) Date of Patent: Jun. 10, 2008

(54) SHRUB PLANT NAMED 'POULTC004'

(50) Latin Name: *Rosa hybrida*
Varietal Denomination: Poultc004

(75) Inventor: Mogens Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 702 days.

(21) Appl. No.: 11/001,948

(22) Filed: Dec. 1, 2004

(51) Int. Cl.
*A01H 5/00* (2006.01)

(52) U.S. Cl. ..... Plt./108

(58) Field of Classification Search ..... Plt./108, Plt./107

See application file for complete search history.

*Primary Examiner*—Annette H Para

(57) ABSTRACT

A new garden rose plant of the shrub rose class which has abundant, red flowers, attractive foliage, and abundant rose hips. This new and distinct variety has shown to be uniform and stable in the resulting generations from asexual propagation.

3 Drawing Sheets

SUMMARY OF THE INVENTION

Botanical classification: *Rosa* hybrid.

Variety denomination: 'Poultc004'.

The present invention constitutes a new and distinct variety of garden rose plant that originated from a controlled crossing between the female seed parent, an unnamed seedling, and the male pollen parent 'Poulerry', a rose variety by the same inventor, described and illustrated in U.S. Plant Pat. No. 13,450.

The two parents were crossed during the summer of 1996, and the resulting seeds were planted in a controlled environment in Fredensborg, Denmark. The new variety is named 'Poultc004'.

The new variety may be distinguished from the female seed parent by the following combination of characteristics:

1. The seed parent has more flower petals than 'Poultc004'.
2. The seed parent is taller in growth habit than 'Poultc004'.

The new variety may be distinguished from its male pollen parent, 'Poulerry' by the following combination of characteristics:

1. The general tonality of flower color for the pollen parent is Red Group 53B to 53D while 'Poultc004', is Red Group 52A.
2. 'Poulerry' has more petals than 'Poultc004'.
3. 'Poulerry' a larger flower diameter than 'Poultc004'.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poultc004' from all other varieties of which we are aware.

As part of the rose development program, Mogens N. Olesen germinated the seeds from the aforementioned hybridization during winter of 1996 and conducted evaluations on the resulting seedlings in a controlled environment in Fredernsborg, Denmark.

'Poultc004' was selected in the spring of 1997 by the inventor as a single plant from the progeny of the aforementioned hybridization.

Asexual reproduction of 'Poultc004' by traditional budding and rooted cuttings was first done by Mogens N. Olesen in the nursery in Fredensborg, Denmark in July 1997. This initial and other subsequent asexual propagations conducted in controlled environments have demonstrated that the characteristics of 'Poultc004' are true to type and are transmitted from one generation to the next.

BRIEF DESCRIPTION OF THE DRAWING

The accompanying color illustrations show as true as is reasonably possible to obtain in color photographs of this type, the typical characteristics of the buds, flowers, leaves, stems, and seeds of 'Poultc004'. Specifically illustrated in the drawings:

FIG. 1.1; Cluster of open flowers;

FIG. 2.1; Flower buds at various stages of development;

FIG. 2.2; Flower petals detached;

FIG. 2.3; Sepals, receptacle, and pedicel;

FIG. 2.4; Mature stem showing prickles;

FIG. 2.5; Mature leaves;

FIG. 3.1; Open flowers and stem showing attachment of peduncles, pedicels, flowers and buds;

FIG. 3.2; Sepals, receptacle, and peduncle;

FIG. 3.3; Detached flower petals;

DETAILED DESCRIPTION OF THE VARIETY

The following is a description of 'Poultc004', as observed in its growth in a field nursery in Jackson County, Oreg.

Observed plants are 2 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poultw001', a rose variety from the same inventors described and illustrated in U.S. Plant Pat. No. 15,111 issued Aug. 24, 2004, are compared to 'Poultc004' in Chart 1.

CHART 1

| | 'Poultc004' | 'Poultw001' |
|---|---|---|
| Color of filaments | Yellow 4B | Yellow Green Group 144D |
| Petal Spot | Yellow 4B | White 155D |
| Petal color upon opening, upper surface. | Red Group 52A. | Red Group 45B |

FLOWER AND FLOWER BUD

Blooming habit: Continuous.

Flower bud:

*Size.*—Upon opening, 18 mm in length from base of receptacle to end of bud. Bud diameter is 11 mm.

*Bud form.*—Ovate.

*Bud color.*—As sepals unfold, petals are Red-Purple Group 57A.

*Sepal inner surface.*—Color: Yellow-Green Group 138B. Surface: Medium amount of pubescence observed.

*Sepal outer surface.*—Color: Yellow-Green Group 144A. Texture: Rough, due to the presence of numerous stipitate glands.

*Sepal shape.*—Apex: Cirrhose. Base: Flat at union with receptacle.

*Sepal margin.*—Margins have weak foliaceous appendages on three of the five sepals.

*Sepal size.*—25 mm (l)×6 mm (w).

*Receptacle.*—Texture: Smooth. Shape: Urn-shaped. Size: 4 mm (h)×4 mm (w). Color: Yellow-Green Group 144A. Anthocyanic pigments the color of Greyed-Orange Group 166A observed.

*Pedicel.*—Length: 25 mm average length. Diameter: 2 mm on average. Color: Yellow-Green Group 144B. Strong anthocyanic pigments Greyed-Orange Group 166A. Strength: Medium strength.

Flower bud development: Flower buds are borne in clusters or racemes with 1 to 5 flowers per flowering branch.

Flower bloom:

*Fragrance.*—None.

*Duration.*—The blooms have a duration on the plant of approximately 7 to 10 days. Petals fall cleanly away from plant after flowers have fully matured.

*Size.*—Flower diameter is 40 to 45 mm when open. Flower depth is 15 mm.

*Flower shape.*—General shape is calathiform with petals that curve out from the center.

*Shape of flower when viewed from the side.*—Upon opening, upper part: Convex. Upon opening, lower part: Flat. Open flower, upper part: Flattened convex. Open flower lower part: Concave.

*Petalage.*—Under normal conditions, flowers have 12 petals total, 2 of which are petaloids.

Petal color:

*Upon opening.*—Outermost and innermost petals: Upper surface: Red Group 52A. Lower surface: Red-Purple Group 58B.

*Basal petal spots, upon opening.*—Upper surface: Yellow Group 4B. Lower surface: Yellow Group 4B.

*After opening.*—Outermost and innermost petals: Upper surface: Red Group 52B. Lower surface: Red-Purple Group 58B.

*Basal petal pots, upon opening.*—Upper surface: Yellow Group 4B. Lower surface: Yellow Group 4B.

General tonality: On open flower Red Group 52A. No change in tonality at the end of the $10^{th}$ day.

Petals:

*Petal reflex.*—Flat.

*Margin.*—Entire and uniform.

*Shape.*—Narrow elliptic. Apex: Rounded. Base: Acute.

*Size.*—25 mm (l)×22 mm (w).

*Texture.*—Smooth.

*Thickness.*—Thin.

Petaloids:

*Quantity.*—Normally 2–3.

*Size.*—17 mm (l)×13 mm (w).

*Shape.*—Asymmetric, narrow elliptical.

*Color.*—Red Group 52B. Red-Purple Group 58B.

Reproductive organs:

*Pollen.*—None observed.

*Anthers.*—Size: 2 mm in length. Color: Greyed-Orange Group 163A. Quantity: 100 on average.

*Filaments.*—Color: Yellow Group 4B. Length: 5 mm.

*Pistils.*—Length: 4 mm. Quantity: 30 on average.

*Stigmas.*—Level in location relative to the length of the filaments and the height of the anthers. Color: Yellow-Green Group 154D.

*Styles.*—Color: Yellow-Green Group 145D at base changing to Red-Purple Group 63B towards the stigma.

*Hips.*—None observed in the field nursery in Jackson County Oreg.

PLANT

Plant growth: Bushy, spreading and moderately compact. When grown as a budded field grown plant on *Rosa multiflora* understock, the average height of the plant is 60 to 100 cm. Plant spread is normally 60 cm.

Stems:

*Color.*—Juvenile growth: Yellow-Green Group 144B. Mature growth: Yellow-Green Group 144A.

*Length.*—On average, canes are 20 to 40 cm from the base of the plant to the flowering portion.

*Diameter.*—12 mm.

*Internodes.*—On mature canes, there is an average distance of 30 mm between nodes.

*Surface texture.*—Young wood: Smooth. Older wood: Smooth.

Prickles:

*Incidence.*—12 prickles per 10 cm of stem on average.

*Shape.*—Upper side: Flat. Lower side: Concave.

*Color.*—Juvenile prickles: Greyed-Red Group 182A. Mature prickles: Greyed-Yellow Group 162B.

Plant foliage: Normal number of leaflets leaves in middle of the stem: 5 to 7 leaflets.

*Compound leaf.*—95 mm (l)×55 mm (w).

*Quantity.*—3 leaves per 10 cm of stem on average.

*Color of mature foliage.*—Upper side: Yellow-Green Group 146A to 147A. Lower side: Yellow-Green Group 146B.

Plant leaves and leaflets:

*Stipules.*—Size: 14 mm in length. Shape: Linear, slightly broad based with outward extending apecies. Margins: Finely serrated with many stipitate glands. Color: Yellow-Green Group 146B.

*Petiole.*—Length: 12 mm. Diameter: 1.5 mm. Upper surface: Color: Yellow-Green Group 146D. Observations: Few stipitate glands. Numerous small prickles. Lower surface: Color: Yellow-Green Group 145A. Observations: Rough.

*Rachis.*—Length: 55 mm average. Upper surface: Color: Yellow-Green Group 146B. Observations: Numerous stipitate glands at margins. Lower surface: Color: Yellow-Green Group 145A. Observations: Numerous small prickles underneath.

*Leaflet.*—Edge: Serrated. Size: Average size of the terminal leaflet on normal leaves is 30 mm (l)×19 mm (w). Shape: Ovate. Base: Obtuse. Apex: Acuminate. Texture: Smooth. Thickness: Average. Arrangement: Odd pinnate. Venation: Reticulate. Glossiness: Glossy.

Disease resistance: Above average resistance to powdery and downy mildew, rust, black spot, and *Botrytis* under normal growing conditions in Jackson County, Oreg.

Cold hardiness:

The variety 'Poultc004' has been found to be cold tolerant to USDA Cold Hardiness Zone 6.

It is claimed:

1. A new and distinct variety of rose plant of the shrub rose class named 'Poultc004', substantially as illustrated and described herein, due to its abundant red flowers, disease resistance, and extended period of bloom.

* * * * *

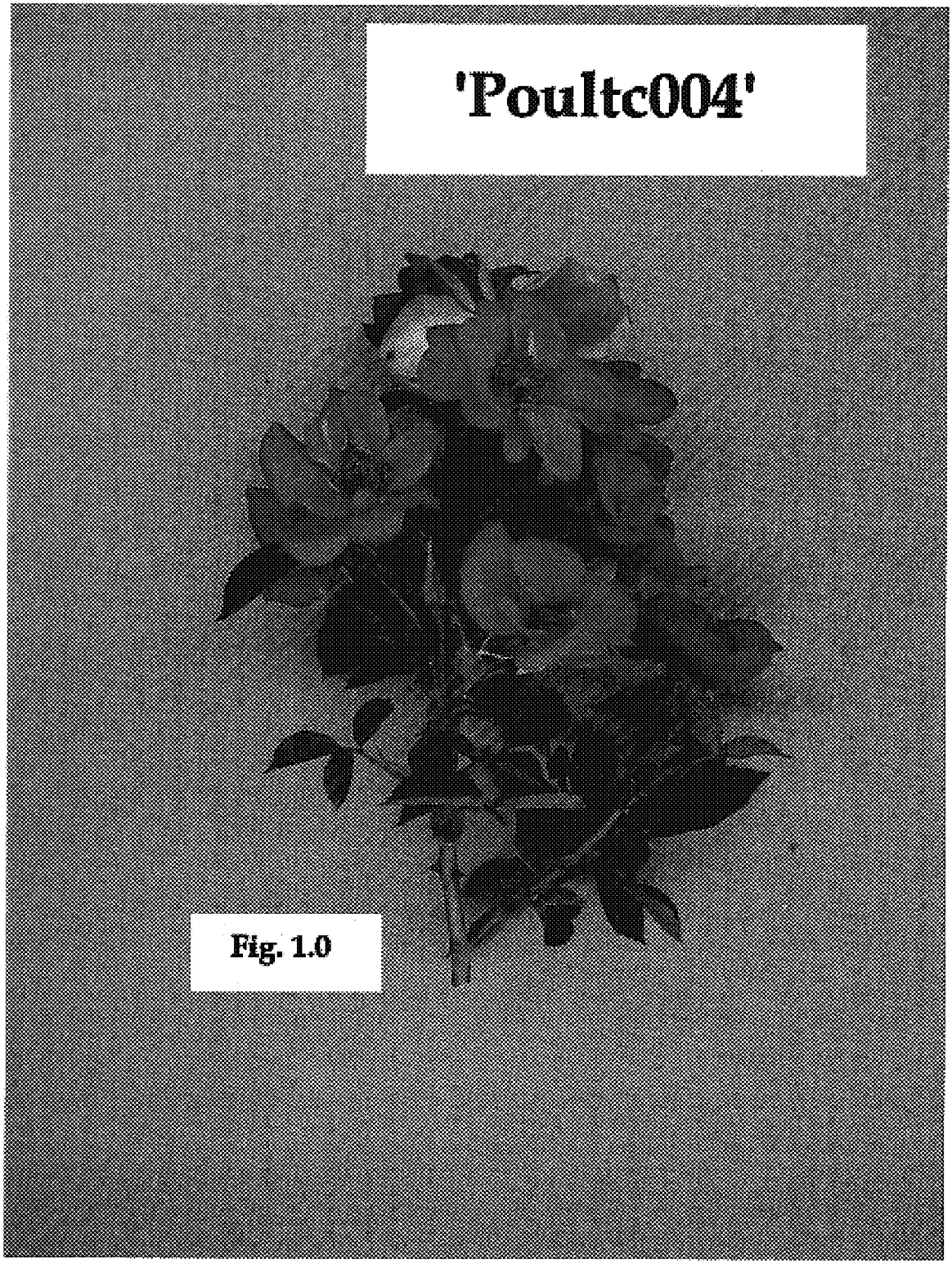
Fig. 1.0

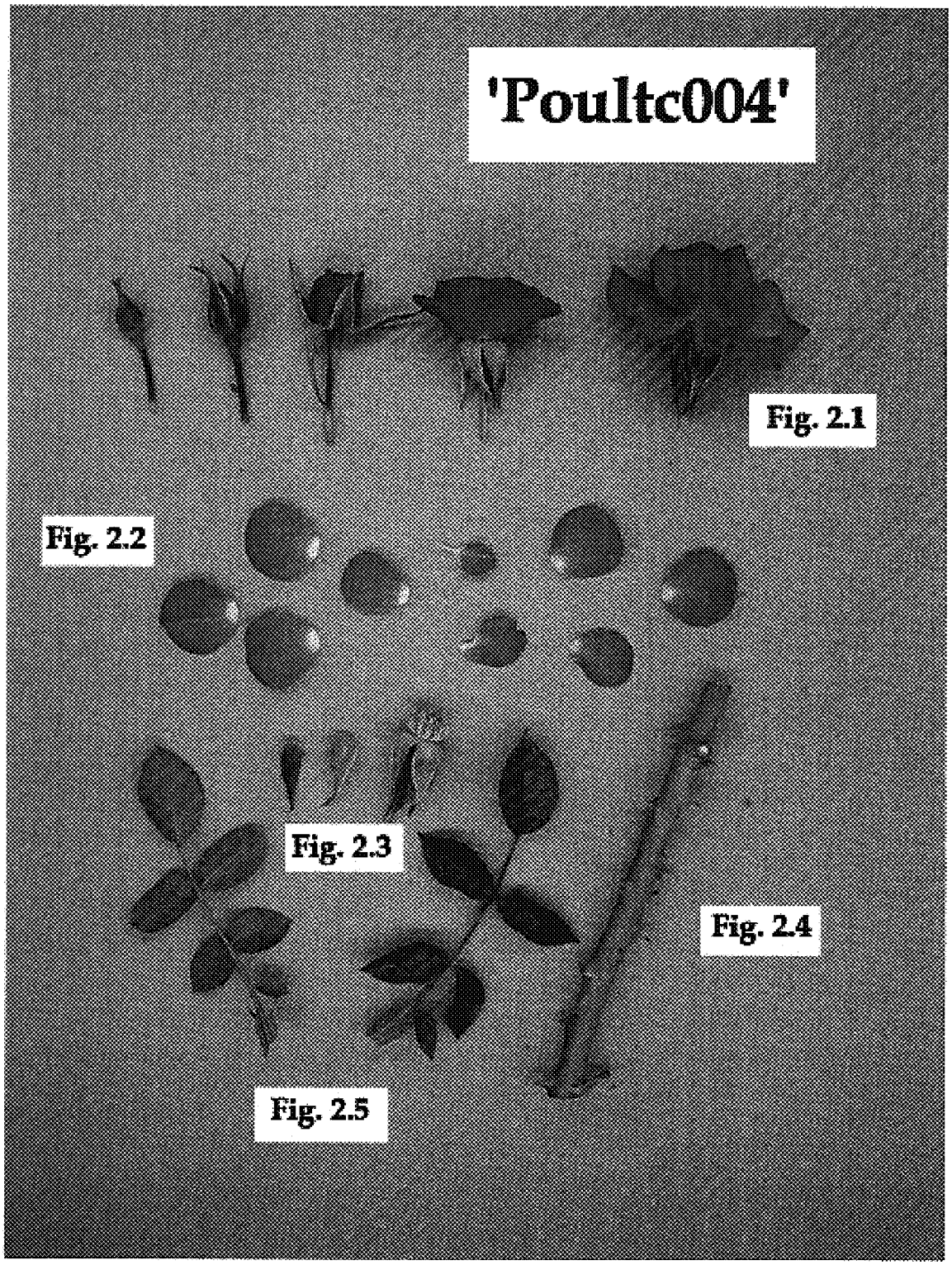
'Poultc004'
Fig. 2.1
Fig. 2.2
Fig. 2.3
Fig. 2.4
Fig. 2.5

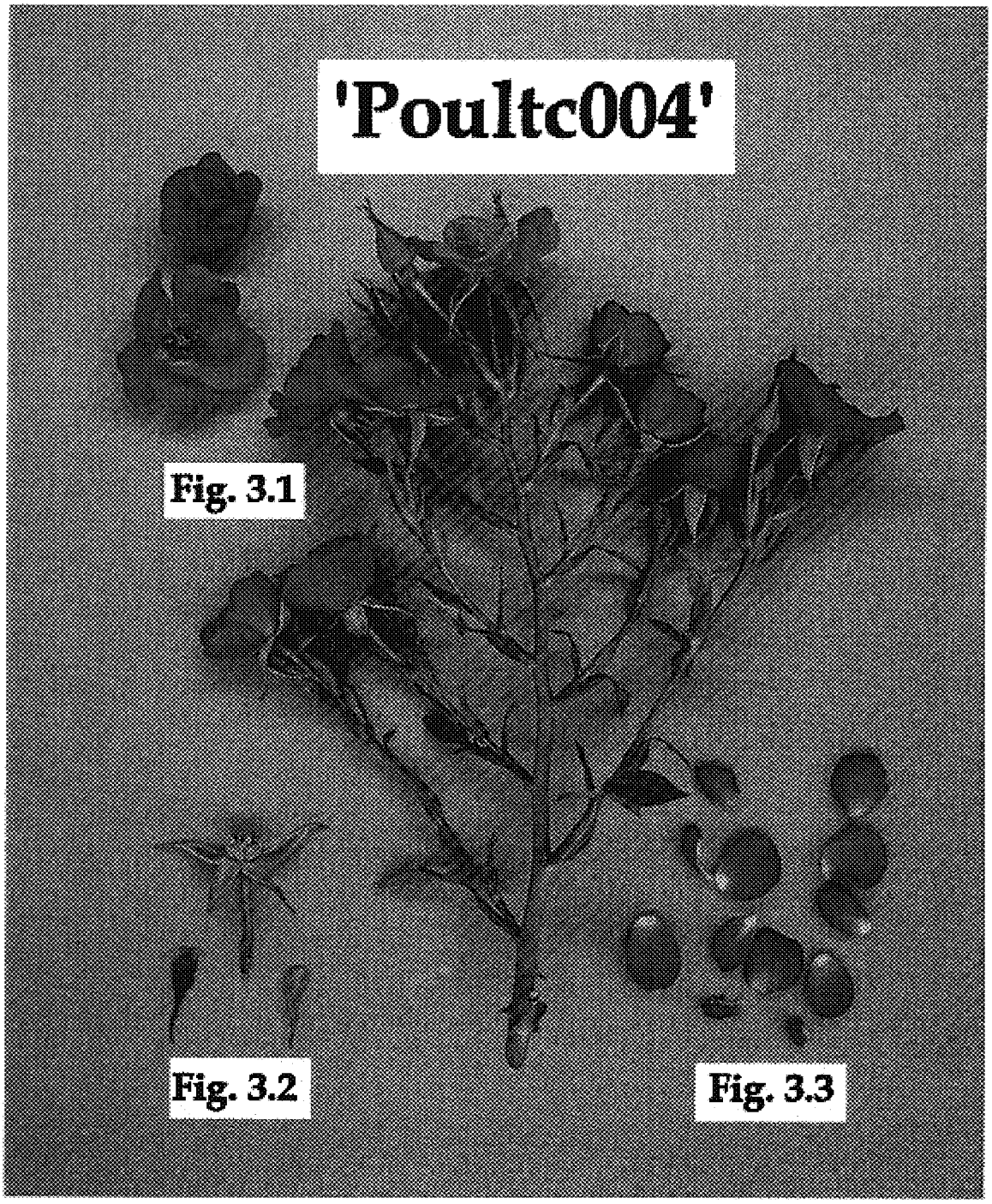
'Poultc004'
Fig. 3.1
Fig. 3.2
Fig. 3.3